(12) United States Patent
Garamszegi (10) Patent No.: US 8,192,438 B2
(45) Date of Patent: Jun. 5, 2012

(54) ROD REDUCER

(75) Inventor: Laszlo Garamszegi, Mission Viejo, CA (US)

(73) Assignee: Phygen, LLC., Irvine, CA (US)

( * ) Notice: Subject to any disclaimer, the term of this patent is extended or adjusted under 35 U.S.C. 154(b) by 1031 days.

(21) Appl. No.: 11/804,723

(22) Filed: May 18, 2007

(65) Prior Publication Data

US 2007/0282337 A1 Dec. 6, 2007

Related U.S. Application Data

(60) Provisional application No. 60/801,339, filed on May 18, 2006.

(51) Int. Cl.
*A61B 17/70* (2006.01)
(52) U.S. Cl. .................................................... 606/86 A
(58) Field of Classification Search ................. 606/86 A
See application file for complete search history.

(56) References Cited

U.S. PATENT DOCUMENTS

| 6,440,133 | B1 | 8/2002 | Beale et al. |
| 6,660,006 | B2 | 12/2003 | Markworth et al. |
| 6,790,209 | B2 | 9/2004 | Beale et al. |
| 7,491,207 | B2 * | 2/2009 | Keyer et al. .................. 606/103 |
| 7,572,281 | B2 * | 8/2009 | Runco et al. .................. 606/279 |
| 7,887,541 | B2 * | 2/2011 | Runco et al. ................. 606/86 A |
| 2004/0049191 | A1 | 3/2004 | Markworth et al. |
| 2005/0261687 | A1 | 11/2005 | Garamszegi et al. |

FOREIGN PATENT DOCUMENTS

WO 2005/102195 11/2005

* cited by examiner

*Primary Examiner* — Eduardo C Robert
*Assistant Examiner* — Ellen C Hammond
(74) *Attorney, Agent, or Firm* — Fred C. Hernandez; Mintz, Levin, Cohn, Ferris, Glovsky and Popeo, P.C.

(57) ABSTRACT

A rod reducer is adapted for inserting a rod into position within an orthopedic device. The rod reducer is configured for use with one hand and does not obstruct the surgeon's view of the surgical field during use.

13 Claims, 6 Drawing Sheets

ROD REDUCER

REFERENCE TO PRIORITY DOCUMENT

This application claims priority of U.S. Provisional Patent Application Ser. No. 60/801,339 filed May 18, 2006. Priority of the aforementioned filing date is hereby claimed and the disclosure of the Provisional Patent Application is hereby incorporated by reference in its entirety.

BACKGROUND

Disclosed is an instrument for moving a part of a surgical implant into position or contact with another surgical implant part. More particularly, disclosed is an instrument for securing a spinal rod to a coupling element.

Spinal fixation surgical techniques use surgical implants and/or mechanical immobilization to fuse two or more vertebral bodies of the spinal column. Spinal fixation may also be used to alter the alignment of adjacent vertebral bodies relative to one another so as to change the overall alignment of the spinal column.

One spinal fixation technique involves immobilizing the spine using orthopedic stabilizing rods, or spine rods. A fixation element, such as a spinal screw, can be threaded into a pedicle of a vertebral body. The spinal screws are generally placed two per vertebra on opposite sides of the spine and serve as anchors for the spine rods. These rods are positioned generally parallel along the length of the spine. Coupling elements adapted for receiving a spine rod therethrough are then used to join the spine rods to the pedicle screws. The spine rod is then held into a seat of the coupling element by way of a set screw or fastener. This process is also known as rod "reduction."

Rod reduction is performed by a surgeon typically using a rod reducing tool to create the necessary pushing and/or pulling forces on the implanted screw and rod. Surgeons can encounter considerable difficulty using these instruments. Many instruments require the use of two hands or have cumbersome mechanisms for urging rods into place. Other limitations of current rod reducing tools include problems with visualization of the surgical field. Handles and triggers used in some instruments block the surgeon's view of the field leading to errors and time lost during the procedure. Still other instruments have a multitude of moving parts with numerous connection points, which can fail as well as add to the cost of manufacturing.

SUMMARY

There is a need for a rod reducer for inserting a rod into position within an orthopedic device that is easy to use with one hand and does not obstruct the surgeon's view of the surgical field. There is a further need for the instrument to be robust, simple in design and have fewer connecting parts to maintain a low cost of manufacturing.

In one aspect, there is disclosed a surgical instrument for reducing a rod toward a bone fastener, comprising: an engaging member extending between a proximal end and a distal end, a distal portion of the engaging member adapted to receive a portion of the rod therein and further adapted to engage a coupling element coupled to the bone fastener; a reducing member movably disposed about the engaging member, the reducing member having a distal end; an actuator assembly mechanically coupled to both the engaging member and to the reducing member, wherein the actuator assembly actuates to move the reducing member distally with respect to the engaging member such that the distal end of the reducing member contacts the rod to move the rod toward the bone fastener; and a handle adapted to actuate the actuator assembly, wherein the engaging member and the reducing member extend along a longitudinal axis and wherein the entire handle is offset from the longitudinal axis.

In another aspect, there is disclosed a surgical instrument for reducing a rod toward a bone fastener, comprising: an engaging member extending between a proximal end and a distal end, a distal portion of the engaging member adapted to receive a portion of the rod therein and further adapted to engage a coupling element coupled to the bone fastener; a reducing member movably disposed about the engaging member, the reducing member having a distal end; an actuator assembly mechanically coupled to both the engaging member and to the reducing member, wherein the actuator assembly actuates to move the reducing member distally with respect to the engaging member such that the distal end of the reducing member contacts the rod to move the rod toward the bone fastener; and a handle adapted to actuate the actuator assembly, wherein the engaging member and the reducing member extend along a longitudinal axis and wherein the longitudinal axis does not intersect any portion of the handle.

Other features and advantages should be apparent from the following description of various embodiments, which illustrate, by way of example, the principles of the invention.

DETAILED DESCRIPTION

Figure 1:
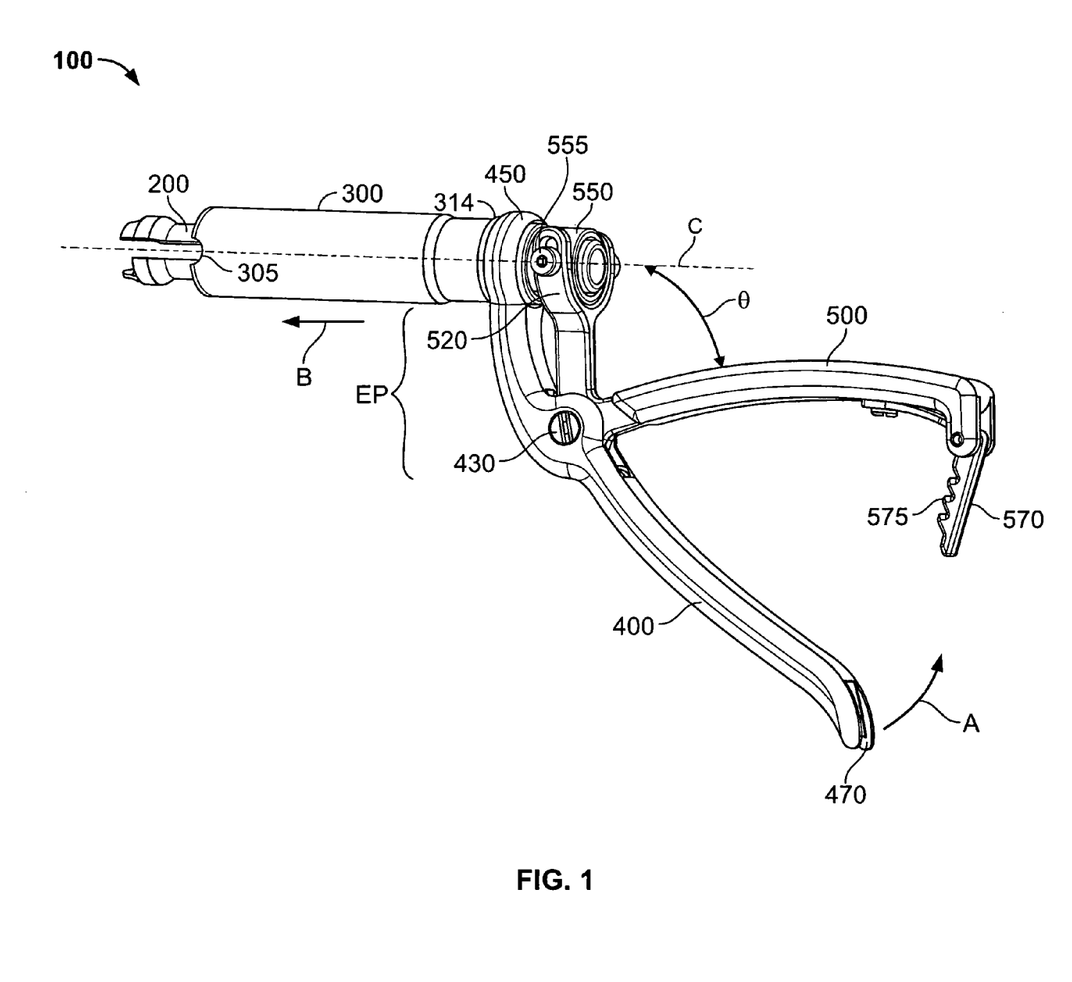
FIG. 1 shows a perspective view of an exemplary instrument for urging a spinal rod into a coupling element in a retracted position.

FIG. 1 shows a perspective view of an exemplary instrument 100 for persuading a rod into a seat recess of an orthopedic device or coupling element, such as a pedicle screw assembly. The instrument 100 includes an inner longitudinal body 200, an outer longitudinal body 300 and a handle or grip made up of a first trigger element 400 and a second trigger element 500. It should be appreciated that the instrument 100 is not limited to the particular mechanical configuration shown in FIG. 1 and that the configuration of the instrument 100 can be modified.

Figure 2:
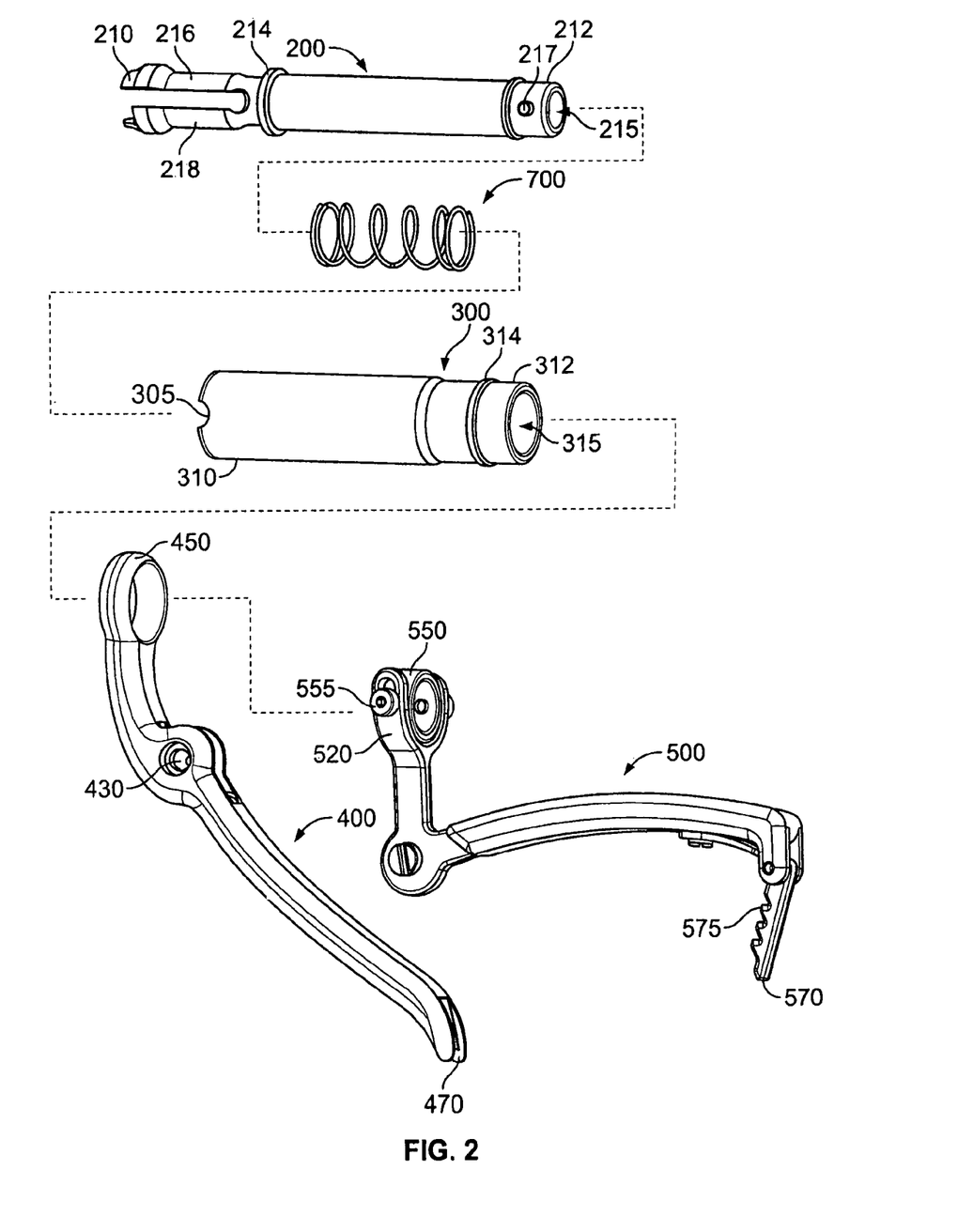
FIG. 2 shows an exploded view of the instrument of FIG. 1.

FIG. 2 shows an exploded view of the exemplary instrument 100 including the inner longitudinal body 200 (also referred to as a reducing member), a spring 700, the outer longitudinal body 300 (also referred to as an engaging member), the first trigger element 400 and the second trigger element 500. The inner longitudinal body 200 is generally cylindrical and has a working end 210 and a trigger end 212. In addition, the inner longitudinal body 200 is generally hollow and defines a channel 215 extending longitudinally through it from the working end 210 to the trigger end 212. The trigger end 212 of the inner longitudinal body 200 includes an aperture 217 through which an attachment element, such as a bolt or screw or the like, may be inserted for attaching it to the second trigger element 500 as described in more detail below. The working end 210 is adapted to mate with a rod. In this regard, the working end 210 can be forked and made up of a pair of opposing prongs 216, 218.

Figure 3:
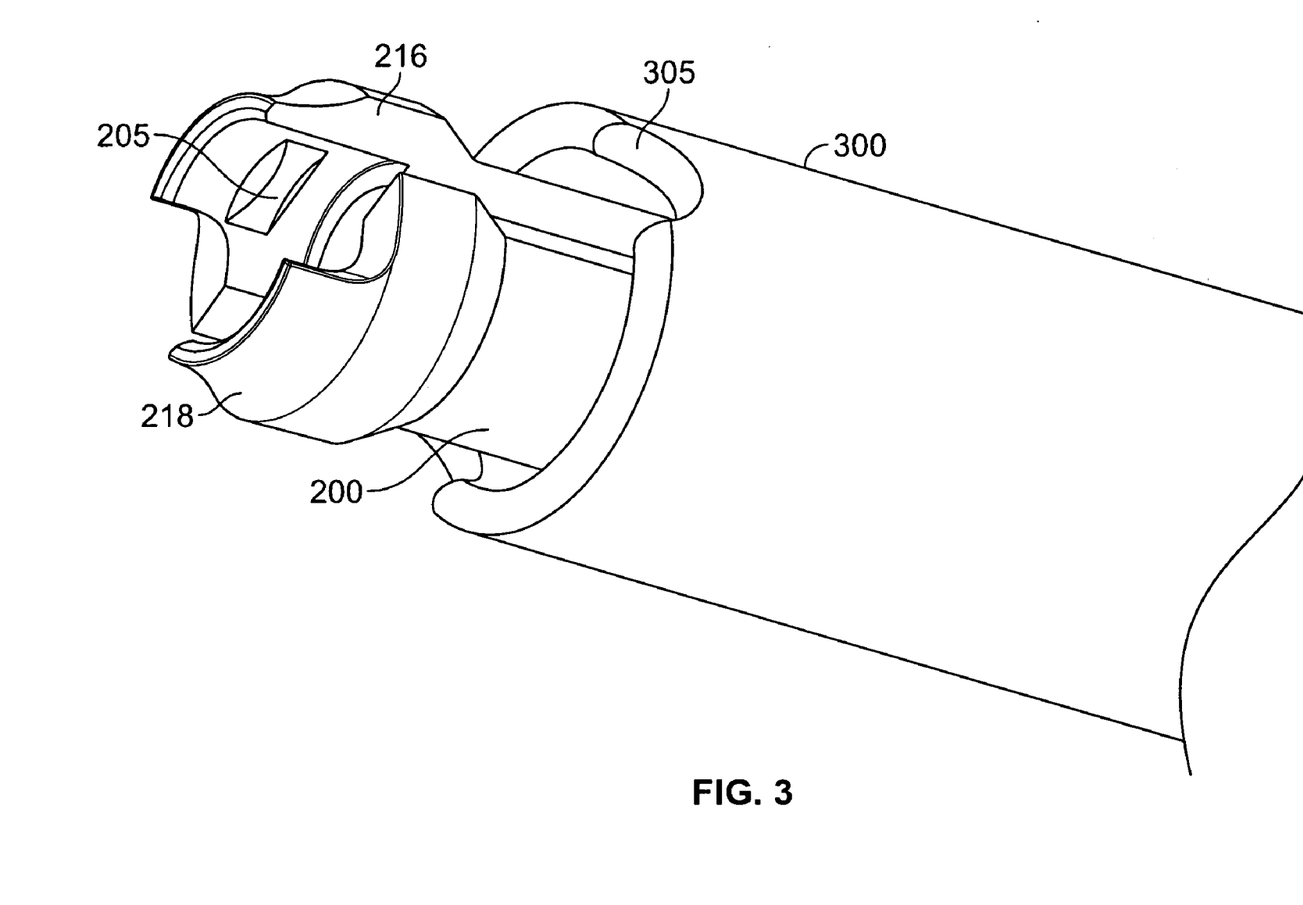
FIG. 3 shows an enlarged, perspective view of a working end of the instrument of FIG. 1 in a partially reduced position.

As best shown in FIG. 3, the prongs 216, 218 each have an interior wall which define catches 205 that are adapted to mate with at least a portion of a pedicle screw assembly. For example, the catches 205 can have a shape that complements or corresponds to the shape of the outer surface of a receiver element or coupling element 220 (see FIG. 5A) of a pedicle screw assembly. The receiver element is sometimes referred to as a yoke. The prongs 216, 218 can be substantially identically configured. They are of a size, shape and depth that allows insertion of a coupling element 220 between them. The prongs 216, 218 are rigid, but sufficiently elastic such that application of force can separate the prongs in order to insert a coupling element 220 between them. The prongs 216, 218 grip the coupling element 220 via spring motion and also due to interaction between the catches 205 and grooves 222 present on the coupling element 220. The inner longitudinal body 200 need not have prongs, but can also be formed from a substantially solid body having an appropriately-shaped socket at its working end 210 for engaging the coupling element 220. The inner longitudinal body 200 can be configured to mate with or couple with other portions of the coupling element 220.

As best shown in FIG. 2, the outer longitudinal body 300 is generally cylindrical and has a working end 310 and a trigger end 312. The working end 310 includes a pair of opposed notches 305. Near the trigger end 312, the outer longitudinal body 300 includes a flange 314. The outer longitudinal body 300 is generally hollow and defines a channel extending longitudinally through it from the working end 310 to the trigger end 312. The outer longitudinal body 300 is sized and shaped to receive the inner longitudinal body 200 therein.

Figure 4:
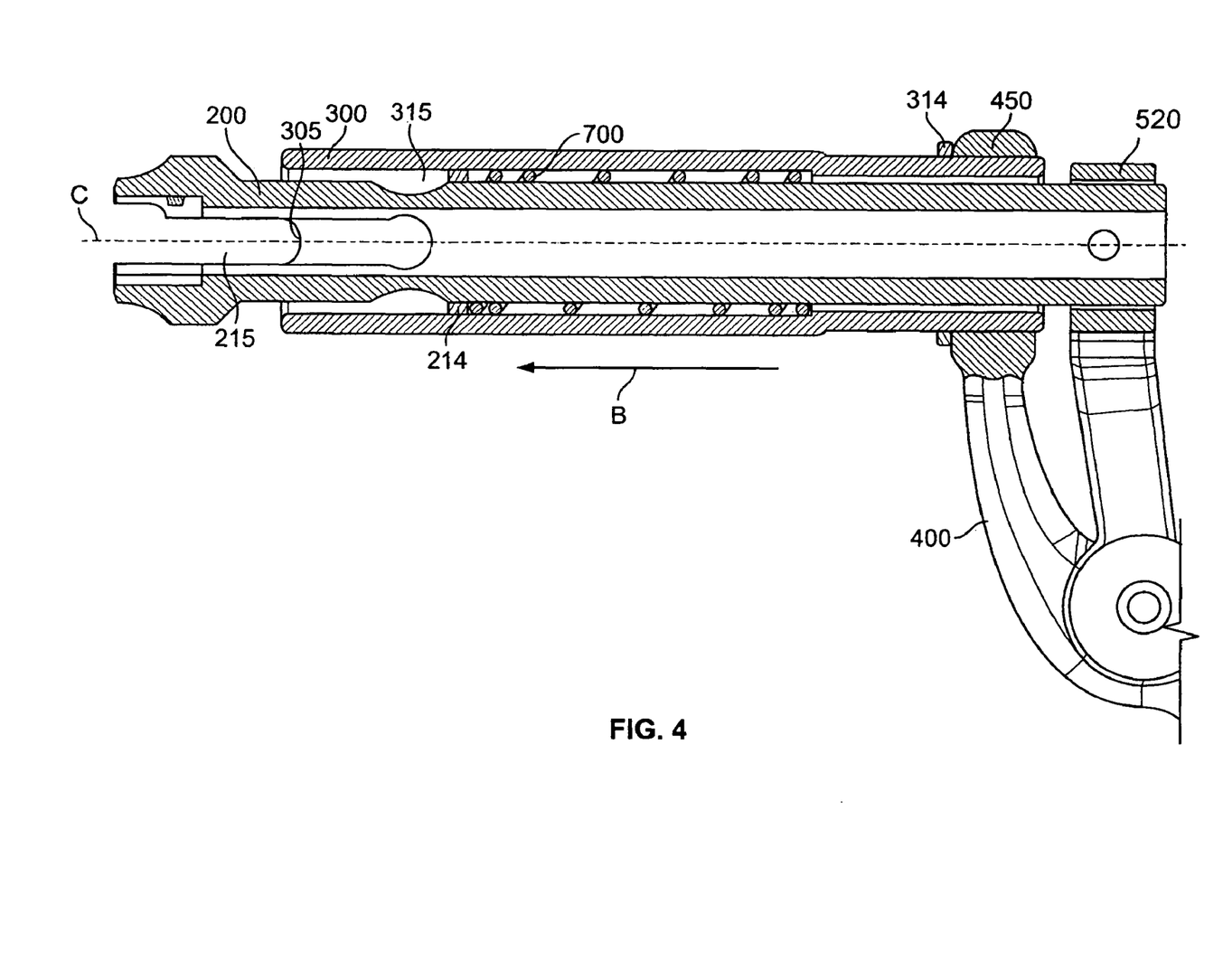
FIG. 4 shows a side, cross-sectional view of the instrument of FIG. 1 in a retracted position.

As shown in FIG. 4, when assembled, the inner longitudinal body 200 is encircled by the spring 700 or other biasing element such that one end of the spring 700 abuts a flange 214 near the working end 210 of the inner longitudinal body 200. The force of the spring 700 results in the instrument 100 being biased toward a retracted position. The spring 700 is disposed between the flange 214 near the working end 210 of the inner longitudinal body 200 and the flange 314 near the trigger end 312 of the outer longitudinal body 300. When not in use, the spring 700 is in the expanded position such that the working end 310 of the outer longitudinal body 300 is positioned away from the working end 210 of the inner longitudinal body 200. For example, the working end 310 of the outer longitudinal body 300 can be at a point furthest away from the working end 210 of the inner longitudinal body 200.

With reference still to FIG. 4, the inner longitudinal body 200 is slidably disposed within the channel 315 of the outer longitudinal body 300. The channel 215 of the inner longitudinal body 200 and the channel 315 of the outer longitudinal body 300 together form a working channel of the instrument 100 which extends along the longitudinal axis C between the trigger ends 212, 312 and working ends 210, 310. The working channel can be used to feed additional parts or tools to the site of the surgical implant. Although the working channel of the instrument 100 is shown as having a generally cylindrical shape, it is to be understood that the instrument working channel can have any appropriate shape. The inner longitudinal body 200 and outer longitudinal body 300 also both extend along the axis C.

The length of the working channel as well as the reduction distance of the instrument 100 can also vary. This allows the surgeon to select an instrument 100 having an extension/passage of appropriate length for the distance of rod reduction that is desired. The inner and outer longitudinal bodies 200, 300 are also shaped such that contact between them is appropriate for being in slideable communication. However, the spacing between the inner and outer longitudinal bodies 200, 300 is minimized to limit the amount of wobble or play between the two.

As mentioned, the instrument 100 has a grip that is made up of a first trigger element 400 and a second trigger element 500 (best shown in FIG. 1). With reference to FIG. 1, the first trigger element 400 includes a coupler, such as a ring 450, at one end that couples or encircles the trigger end 312 of the outer longitudinal body 300. The second trigger element 500 has a fork 520 in which another coupler, such as a ring 550, is rotatably attached via an attachment element 555. The ring 550 encircles the trigger end 212 of the inner longitudinal body 200 and is attached via the attachment element 555 threaded through the aperture 217 located near the trigger end 212 of the inner longitudinal body 200. The ring 450 of the first trigger element 400 is disposed between the flange 314 and the ring 550 of the second trigger element 400.

It should be noted that the use of attachment elements, such as bolts and screws, in the construction of the instrument 100 are at a minimum. This reduces the number of connection points and thereby confers a more robust construction to the instrument. Most parts are machined to connect and fit together as opposed to being bolted or screwed together. The parts of the instrument 100 are made of a sturdy, biocompatible material such as stainless steel using standard fabrication techniques for medical grade instruments. Other biocompatible materials are contemplated.

The second trigger element 500 is at an angle θ from the longitudinal axis C of the instrument 100. This offset of the second trigger element 500 from the longitudinal axis C of the instrument 100 allows for a substantially unimpeded view of the surgical site by the operator during use. This is in contrast to instruments commonly used in the art which are not offset from the longitudinal axis of the instrument. Instruments where the handle or actuator means are not offset block at least a part of the surgeon's view of the surgical field. However, it should be understood that angle θ can be other angles such that the surgeon's view of the surgical field is substantially unimpeded by the instrument handles and trigger elements. In an embodiment, the entire handle is offset from the axis C. The entire handle can be offset to one side of the axis C. The handle can include an elongate portion EP that extends laterally away from the axis C and positions the entire handle in an offset position relative to the axis C. The handle can be configures such that no portion of either of the trigger elements 400 and 500 intersects the axis.

Figure 5A:
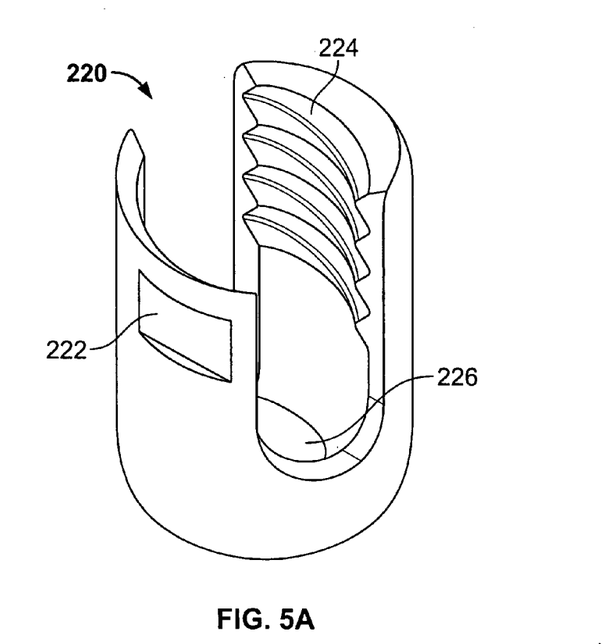
FIG. 5A shows a perspective view of a coupling element.

The instrument 100 can be used to urge a rod into a coupling element, such as a coupling element of a pedicle screw assembly. FIG. 5A shows an exemplary coupling element 220. The coupling element 220 includes grooves 222 on its outer surface, threads 224 on its inner surface and an aperture 226 through which a fastener, such as a pedicle screw, can be inserted. The fastener can be a multi-axial or uni-axial screw, a hook, or other bone or tissue engaging device. The coupling element 220 has slots in which the rod can be positioned. The threads 224 are configured for a set screw or the like (not shown) to be tightened over the rod securing it in the coupling element 220.

Figure 5B:
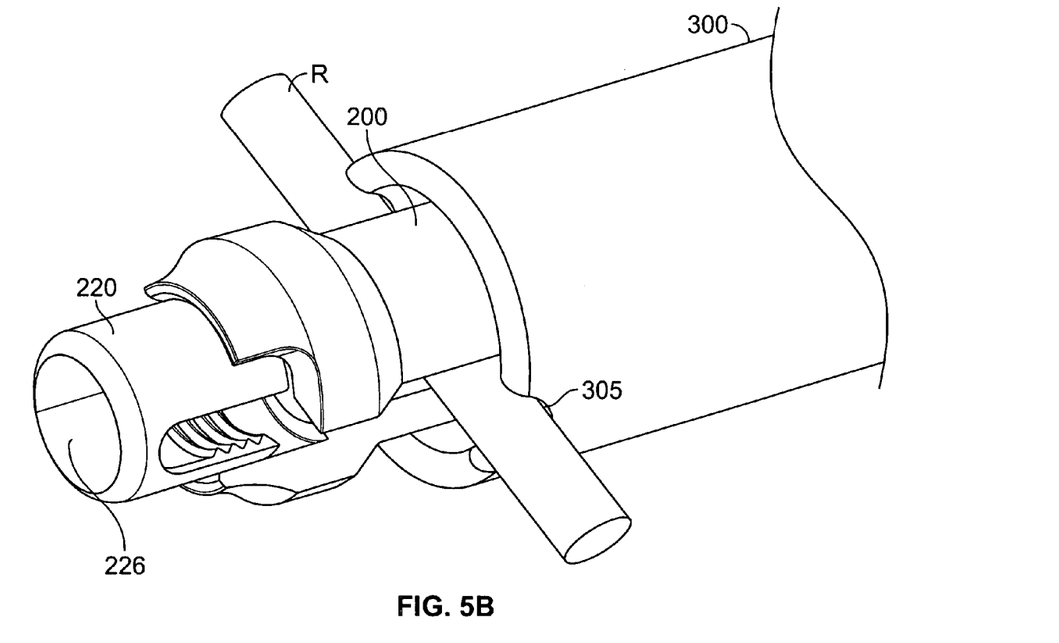
FIG. 5B shows an enlarged, perspective view of the working end of the instrument of FIG. 3 engaged with a rod and coupling element shown in a retracted position.

FIG. 5B shows a rod R and coupling element 220 engaged at the working end of the instrument 100 such as engaged to the member 200. The rod R rests within the notches 305 of the outer longitudinal body 300. The coupling element 220 is shown within the grip of the prongs 216, 218 of the inner longitudinal body 200. The rod R can be any elongated implant element of any size or shape so long as it can be secured to the coupling element 220.

With reference again to FIG. 1, the instrument 100 can further include a ratchet mechanism 570. As described above, the instrument 100 is biased in the retracted position such that the working end 310 of the outer longitudinal body 300 is positioned away from, such as at a point furthest away from, the working end 210 of the inner longitudinal body 200 by virtue of the force of the spring 700 disposed between the flanges 314 and 214. As the outer longitudinal body 300 slides longitudinally across the inner longitudinal body 200 in the direction of arrow B (FIG. 4) to reduce the rod, the spring 700 compresses between the flanges 314 and 214. The ratchet mechanism 570 is used to hold the instrument 100 in this reduced position.

With reference still to FIG. 1, the second trigger element 500 has a ratchet mechanism 570 and the first trigger element 400 has a connector 470. The teeth 575 of the ratchet mechanism 570 cooperate with the connector 470 as the trigger element 400 is squeezed toward the trigger element 500 in the direction of arrow A and the two are brought together. The teeth 575 can be step-wise engaged with the connector 470. The outer longitudinal body 300 is advanced in the direction of arrow B as successive teeth 575 engage with the connector 470. As this process continues and the notch 305 of the outer longitudinal body 300 contacts the rod R, the rod R is urged into position in the coupling element 220. The ratchet mechanism 570 locks the position of the outer longitudinal body 300 with respect to the inner longitudinal body 200 and prevents regression of the rod R back away from the coupling element 220 in the direction opposite of arrow B. The operator thus is not required to continue applying pressure to the trigger elements to maintain position of the rod.

In operation, the user grasps the instrument 100 in one hand at the first and second trigger elements. The coupling element 220 is engaged between the prongs 216, 218 of the inner longitudinal body 200. The rod R is resting between the notches 305 and the coupling element 220. The first trigger element 400 is moved or squeezed toward the second trigger element 500 in the direction of arrow A (see FIG. 1) around pivot point 430. The process can be a single, continuous movement or alternatively can be step-wise due to the use of a ratchet mechanism 570 as described above. The displacement of the first trigger element 400 around pivot point 430 causes movement of the outer longitudinal body 300 slidably over the inner longitudinal body 200 in the direction of arrow B. As the outer longitudinal body 300 slides forward, the notches 305 connect with the rod R and urge the rod R in the direction of arrow B. The coupling element 220 is held or gripped between the prongs 216, 218 at the working end 210 of the inner longitudinal body 200. The rod R is urged or advanced into the recess or seat of the coupling element 220. Outward movement of the prongs 216, 218 is prevented due in part to the presence of the outer longitudinal body 300 over the working end 210 of the inner longitudinal body 200.

Once the desired rod reduction is achieved, the rod R is secured in place. To secure the rod in place, a fastener, such as a set screw, can be inserted through the working channel of the instrument 100. The set screw is tightened into the threads 224 of the coupling element 220 by a driver or other tool similarly fed through the working channel of the instrument 100.

The instrument 100 can release its grip by rotation to disengage the catches 205 from the grooves 222 in the outer surface of the coupling element 220. Force can be applied to the instrument 100 in the direction opposite of the secured rod R. This frees the instrument 100 from its grip on the coupling element 220 while leaving the secured rod R in place.

Figure 6:
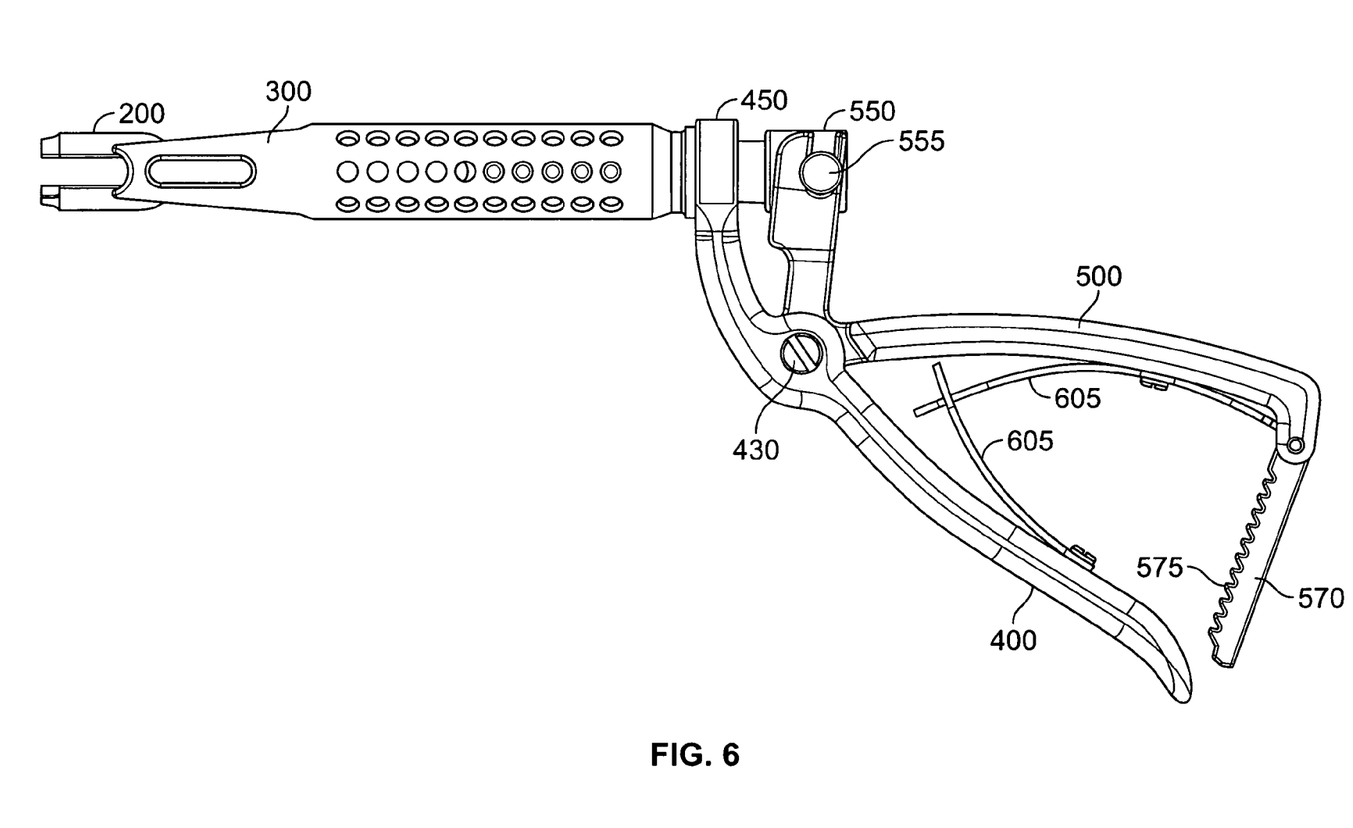
FIG. 6 shows a side view of another embodiment of the instrument.

FIG. 6 shows a side view of another embodiment of the instrument 100. This embodiment of the instrument 100 is substantially similar to the previous embodiment. For example, the instrument 100 includes an inner longitudinal body 200, an outer longitudinal body 300 and a handle or grip made up of a first trigger element 400 and a second trigger element 500. The outer longitudinal body 300 includes a plurality of apertures or holes along its length that communicate with an internal, elongate channel. Like numerals refer to like parts with respect to the previous embodiment of the instrument 100.

The previous embodiment of the instrument 100 included a biasing element comprised of a spring 700 (FIGS. 2 and 4) that provided a biasing force that urged the instrument toward a retracted position. In the embodiment of FIG. 6, the spring 700 is replaced by a biasing element comprised of one or more leaf springs 605 that are positioned between the triggers 400 and 500. The leaf springs 605 provide a biasing force that urges the triggers 400 and 500 away from one another. Thus, the leaf springs 605 urge the instrument toward a retracted position. It should be appreciated that any of a variety of mechanisms or other means can be used to urge the instrument toward the retracted position. Alternately, the instrument is urged toward a non-retracted position.

Although embodiments of various methods and devices are described herein in detail with reference to certain versions, it should be appreciated that other versions, embodiments, methods of use, and combinations thereof are also possible. Therefore, the spirit and scope of the instrument should not be limited to the description of the embodiments contained herein.

What is claimed:

1. A surgical instrument for reducing a rod toward a bone fastener, comprising:
    an inner longitudinal body extending between a proximal end and a distal end, a distal portion of the inner longitudinal body adapted to receive a portion of the rod therein and further adapted to engage a coupling element coupled to the bone fastener;
    an outer longitudinal body movably disposed about the inner longitudinal body, the outer longitudinal body having a distal end;
    an actuator assembly mechanically coupled to both the inner longitudinal body and to the outer longitudinal body, wherein the actuator assembly actuates to move the outer longitudinal body distally with respect to the inner longitudinal body such that the distal end of the outer longitudinal body contacts the rod to move the rod in the coupling element toward the bone fastener; and
    a handle adapted to actuate the actuator assembly, the handle having a first arm coupled with the inner longitudinal body and a second arm attached to a proximal portion of the outer longitudinal body at an attachment point, the first and second arms being rotatable about a common axis to move the outer longitudinal body relative to the inner longitudinal body, wherein the inner longitudinal body and the outer longitudinal body extend along a longitudinal axis and wherein the common axis does not intersect the longitudinal axis;

wherein the outer longitudinal body extends about the inner longitudinal body from the attachment point to the distal end of the outer longitudinal body.

2. An instrument as in claim 1, wherein the entire handle is offset to one side of the longitudinal axis.

3. An instrument as in claim 1, wherein the first arm is pivotally coupled to the inner longitudinal body and the second arm is pivotally coupled to the outer longitudinal body.

4. An instrument as in claim 1, wherein the inner longitudinal body defines an internal shaft that extends along the longitudinal axis, the internal shaft sized to receive a portion of a pedicle screw assembly.

5. An instrument as in claim 1, wherein the handle includes a ratchet mechanism adapted to fix the position of the inner longitudinal body relative to the reducing member.

6. An instrument as in claim 1, wherein the actuator assembly is pivotally coupled to the inner longitudinal body and pivotally coupled to the outer longitudinal body.

7. A surgical instrument for reducing a rod toward a bone fastener, comprising:
- an inner longitudinal body extending between a proximal end and a distal end, a distal portion of the inner longitudinal body adapted to receive a portion of the rod therein and further adapted to engage a coupling element coupled to the bone fastener;
- an outer longitudinal body movably disposed about the inner longitudinal body, the outer longitudinal body having a distal end;
- an actuator assembly mechanically coupled to both the inner longitudinal body and to the outer longitudinal body, wherein the actuator assembly actuates to move the outer longitudinal body distally with respect to the inner longitudinal body such that the distal end of the outer longitudinal body contacts the rod to move the rod in the coupling element toward the bone fastener; and
- a handle adapted to actuate the actuator assembly, the handle having a first arm that actuates the inner longitudinal body and a second arm that actuates, and is attached at an attachment point to, the outer longitudinal body, the first and second arms being rotatable about a common axis, wherein the inner longitudinal body and the outer longitudinal body extend along a longitudinal axis and wherein the longitudinal axis does not intersect the common axis;

wherein the outer longitudinal body extends about the inner longitudinal body from the attachment point to the distal end of the outer longitudinal body.

8. An instrument as in claim 7, wherein the entire handle is offset to one side of the longitudinal axis.

9. An instrument as in claim 7, wherein the first arm is pivotally coupled to the inner longitudinal body and the second arm is pivotally coupled to the outer longitudinal body.

10. An instrument as in claim 7, wherein the inner longitudinal body defines an internal shaft that extends along the longitudinal axis, the internal shaft sized to receive a portion of a pedicle screw assembly.

11. An instrument as in claim 7, wherein the handle includes a ratchet mechanism adapted to fix the position of the inner longitudinal body relative to the outer longitudinal body.

12. An instrument as in claim 7, wherein the actuator assembly is pivotally coupled to the inner longitudinal body and pivotally coupled to the outer longitudinal body.

13. An instrument as in claim 7, wherein the inner longitudinal body grips the coupling element.

* * * * *